US00PP18145P3

(12) United States Plant Patent
Olesen

(10) Patent No.: US PP18,145 P3
(45) Date of Patent: Oct. 30, 2007

(54) COMPACT FLORIBUNDA ROSE PLANT NAMED 'POULPAL021'

(50) Latin Name: *Rosa hybrida*
Varietal Denomination: Poulpal021

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 25 days.

(21) Appl. No.: 11/389,470

(22) Filed: Mar. 23, 2006

(65) Prior Publication Data

US 2007/0226853 P1 Sep. 27, 2007

(51) Int. Cl.
*A01H 5/00* (2006.01)

(52) U.S. Cl. ..... Plt./142

(58) Field of Classification Search ..... Plt./142
See application file for complete search history.

*Primary Examiner*—Anne Marie Grunberg
*Assistant Examiner*—S. B. McCormick-Ewoldt

(57) ABSTRACT

A new garden rose plant of the floribunda rose class which has abundant, red flowers and attractive foliage. This new and distinct variety has shown to be uniform and stable in the resulting generations from asexual propagation.

1 Drawing Sheet

Botanical classification: *Rosa hybrida.*
Variety denomination: 'Poulpal021'.

SUMMARY OF THE CLAIMED PLANT

The present invention constitutes a new and distinct variety of garden rose plant that originated from a controlled crossing between the female seed parent, an unnamed seedling, and the male pollen parent, 'Poulgrad' described in U.S. Pat. No. 11,610.

The two parents were crossed during the summer of 1997, and the resulting seeds were planted in a controlled environment in Fredensborg, Denmark. The new variety is named 'Poulpal021'.

The new variety may be distinguished from the female seed parent by the following combination of characteristics:

1. The seed parent has medium pink flowers. 'Poulpal021' has dark red flowers.
2. The seed parent has a petal count of 25 to 40 petals, while 'Poulpal021' has 180 petals.

The new variety may be distinguished from its male pollen parent, by the following combination of characteristics:

1. General tonality for 'Poulgrad' open flower color is Red Group 53A with intonations of 46A. 'Poulpal021' is Red Group 53A with intonations of Red-Purple Group 60A.
2. 'Poulgrad' has a flower diameter of 35 mm. 'Poulpal021' flowers are is 42 mm in diameter.
3. 'Poulpal21' has more than double the amount of flower petals than 'Poulgrad'.

The objective of the hybridization of this rose variety was to create a new and distinct variety for garden use with unique qualities, such as:

1. Uniform and abundant red flowers which do not fade as flowers mature;
2. Vigorous, but compact growth;

3. Disease resistance;
4. High petal count.

This combination of qualities is not present in previously available commercial cultivars of this type, known to the inventors, and distinguish 'Poulpal021' from all other varieties of which we are aware.

As part of the rose development program, Mogens N. Olesen germinated the seeds from the aforementioned hybridization during winter of 1997 and conducted evaluations on the resulting seedlings in a controlled environment in Fredensborg, Denmark.

'Poulpal021' was selected in the spring of 1998 by the inventor as a single plant from the progeny of the aforementioned hybridization.

Asexual reproduction of 'Poulpal021' by traditional budding and rooted cuttings was first done by Mogens N. Olesen in the nursery in Fredensborg, Denmark in July 1998. This initial and other subsequent asexual propagations conducted in controlled environments have demonstrated that the characteristics of 'Poulpal021' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulpal021'. Specifically illustrated in the drawing.

DETAILED DESCRIPTION OF THE VARIETY

Figures 1A, 1B, 1C, 1D, 1E, 1F, 1G:
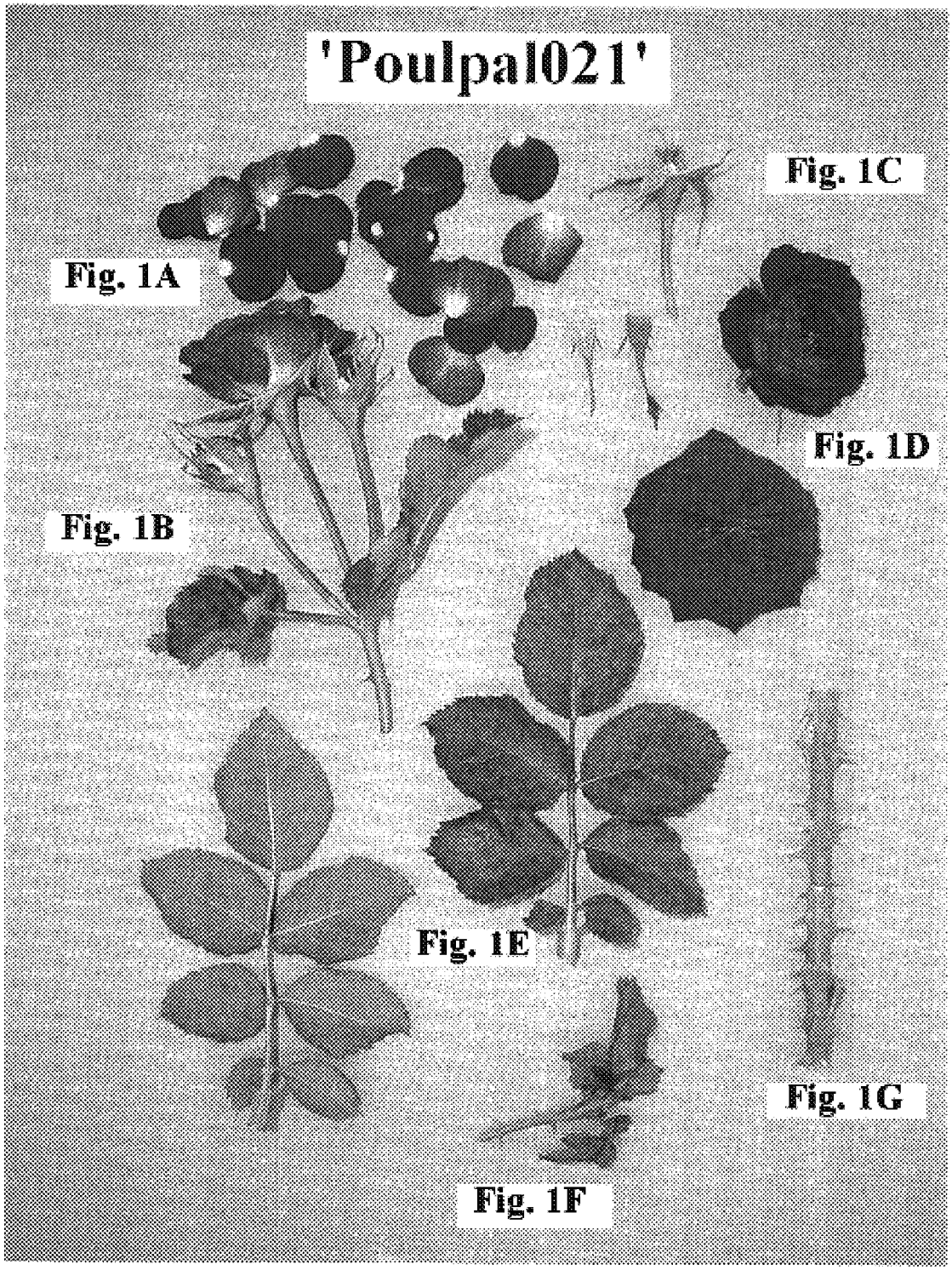
FIG. 1A; Flower petals, detached.
FIG. 1B; Cluster of flowers at various stages of opening attached to stem, showing pedicels receptacles, and attachment of leaves.
FIG. 1C; Sepals, receptacle, and peduncle.
FIG. 1D; Fully open flowers.
FIG. 1E; Mature leaves.
FIG. 1F; Juvenile growth, exhibiting anthocyanin.
FIG. 1G; Bare stem exhibiting thorns.

The following is a description of 'Poulpal021', as observed in its growth in a field nursery in Jackson County, Oreg. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulchris', a rose variety from the same inventors described and illustrated in U.S. Plant Pat. No. 11,151 issued Dec. 14, 1999, are compared to 'Poulpal021' in Chart 1.

CHART 1

| | 'Poulpal021' | 'Poulchris' |
|---|---|---|
| Petal count | 180 | 55 to 65 |
| Normal number of leaflets on compound leaves | 7 | 5 |
| Petal color, upper surface. | Red Group 53A to Red-Purple Group 60A. | Red Group 53A. |

FLOWER AND FLOWER BUD

Blooming habit: Continuous.

Flower bud:

*Size.*—Upon opening, 23 mm in length from base of receptacle to end of bud. Bud diameter is 14 mm.

*Bud form.*—Ovate.

*Bud color.*—As sepals unfold, petals are Red Group 53B.

*Sepal inner surface.*—Color: Yellow-Green Group 146B. Surface: Medium pubescence observed.

*Sepal outer surface.*—Color: Yellow-Green Group 146A and Yellow-Green Group 144A. Texture: Smooth.

*Sepal shape.*—Apex: Cirrhose. Base: Flat at union with receptacle.

*Sepal margin.*—Margins have medium foliaceous appendages on three of the five sepals.

*Sepal size.*—32 mm (l)×8 mm (w).

*Receptacle.*—Texture: Smooth. Shape: Funnel shaped. Size: 11 mm (h)×10 mm (w). Color: Yellow-Green Group 144A.

*Pedicel.*—Surface: Smooth with few stipitate glands. Length: 50 to 60 mm. Diameter: 3 mm on average. Color: Yellow-Green Group 144A. Anthocyanic pigments Greyed-Orange 177A. Strength: Very strong.

Flower bud development: Occasionally singularly. Normally, flowers buds are borne in clusters of 5 to 9 flower buds per stem. Inflorescence type is a corymb.

Flower bloom:

*Fragrance.*—None.

*Duration.*—The blooms have a duration on the plant of approximately 12 days. After flowers have fully matured, petals are somewhat tenacious.

*Size.*—Flower diameter is 50 mm when open. Flower depth is 23 mm.

*Flower shape.*—A rosette with petals tightly packed in to sections.

*Shape of flower, side view.*—Upon opening, Upper portion: Flat. Lower portion: Flat. After opening, Upper portion: Flattened convex. Lower portion: Concave.

*Petalage.*—Normally, flowers have an average of 180 petals total, 20 to 25 of which are petaloids.

Petal color:

*Upon opening, outer petals.*—Upper surface: Red Group 53A with intonations of Red-Purple Group 60A. Lower surface: Red-Purple Group 61B with radial streaks of yellow-Green Group 150D to White Group 155A at basal to middle zone.

*Upon opening, inner petals.*—Upper surface: Red Group 53A with intonations of Red-Purple Group 60A. Lower surface: Red-Purple Group 61B.

*Basal petal spots, upon opening.*—Upper surface: Yellow Group 4C. Lower surface: Yellow Group 4C and 4D.

*After opening, outer petals.*—Upper surface: Red Group 53A with intonations of Red-Purple Group 60A. Lower surface: Red-Purple Group 61B with radial streaks of yellow-Green Group 150D to White Group 155A at basal zone, extending to the middle zone.

*Upon opening, inner petals.*—Upper surface: Red Group 53A with intonations of Red-Purple Group 60A. Lower surface: Red-Purple Group 61B.

*Basal petal spots, upon opening.*—Upper surface: Yellow Group 4C. Lower surface: Yellow Group 4C and 4D.

General tonality: On open flower Red Group 53A with intonations of Red-Purple Group 60A. No change in the general tonality at the end of the $7^{th}$ to 10th day. Afterwards, general tonality is Red Group 46B.

Petals:

*Petal reflex.*—None.

*Margin.*—Medium undulations of margin observed.

*Shape.*—Generally broad elliptical. Apex: Orbicular. Base: Acute.

*Size.*—Innermost petals: 8 mm (l)×5 mm (w). Outermost petals: 27 mm (l)×25 mm (w).

*Texture.*—Smooth.

*Thickness.*—Average.

Petaloids:

*Quantity.*—20 to 25.

*Shape.*—Elliptical with narrowly acute base.

*Color.*—Red-Purple 64D with streaks of Green-White Group 157D bisecting the petaloids.

*Size.*—7 mm (l)×4 mm (w).

Reproductive organs:

*Pollen.*—None observed.

*Anthers.*—Size: 2 mm in length. Color: Yellow-Orange Group 22A. Quantity: 35 average.

*Filaments.*—Color: Yellow Group 4D. Length: 5 mm.

*Pistils.*—Length: 10 to 13 mm. Quantity: Normally 70 to 80.

*Stigmas.*—Superior in location relative to the length of the filaments and the height of the anthers. Color: Yellow-White Group 158A.

*Styles.*—Color: White Group 155B at base with Red-Purple Group 60C toward the upper portion.

*Hips.*—None observed in the field nursery in Jackson County Oreg.

PLANT

Plant growth: Moderate, upright to bushy. When grown as a budded field grown plant on *Rosa multiflora* understock, the average height of the plant is 50 cm. Spread is generally 40 cm.

Stems:

*Color.*—Juvenile growth: Yellow-Green Group 144B. Mature growth: Green Group 137C.

*Length.*—On average, canes are 30 cm from the base of the plant to the flowering portion.

*Diameter.*—5 mm.

*Internodes.*—On mature canes, there is an average distance of 35 mm between nodes.

*Surface texture.*—Young wood: Smooth. Older wood: Rough with many small prickles.

Thorns:

*Incidence.*—30 thorns per 10 cm of stem on average.

*Size.*—4 mm in length.

*Shape.*—Upper side: Concave. Lower side: Deeply concave.

*Color.*—Juvenile thorns: Greyed-Red Group 180A with intonations of between Yellow-White Group 158A and Yellow-Green Group 144C. Mature thorns: Yellow-Green Group 144B with intonations of Greyed-Yellow Group 160C.

Plant foliage: Normal number of leaflets leaves in middle of the stem: 7 leaflets.

*Compound leaf.*—120 mm (l)×90 (w).

*Quantity.*—2 leaves per 10 cm of stem on average.

*Color of mature foliage.*—Upper side: Yellow-Green Group 147A. Lower side: Yellow-Green Group 147B.

*Color of juvenile foliage.*—Upper side: Yellow-Green Group 146C with anthocyanic intonations of Greyed-Purple 183A. Lower side: Yellow-Green Group 146C with anthocyanic intonations of Greyed-Purple 183A.

Plant leaves and leaflets:

*Stipules.*—Size: 27 mm in length. Shape: Linear, slightly broad based with outward extending apecies. Margins: Finely serrated with stipitate glands. Color: Green Group 137A.

*Petiole.*—Length: 28 mm. Diameter: 2 mm. Upper surface: Color: Yellow-Green Group 145C. Lower surface: Color: Yellow-Green Group 145B. Observations: Few stipitate glands. Few small prickles observed.

*Rachis.*—Length: 45 mm. Upper surface: Color: Yellow-Green Group 145C. Lower surface: Color: Yellow-Green Group 145B. Observations: Few stipitate glands. Few small prickles observed.

*Leaflets.*—Margins: Serrated. Size: Average size of the terminal leaflet on normal leaves is 53 mm (l)×42 mm (w). Shape: Generally elliptical to orbicular. Base: Rounded. Apex: Cuspidate. Texture: Smooth. Thickness: Average. Arrangement: Odd pinnate. Venation: Reticulate. Glossiness: Matte.

Disease resistance: Above average resistance to powdery and downy mildew, rust, black spot, and *Botrytis* under normal growing conditions in Jackson County, Oreg.

Cold hardiness: The variety 'Poulpal021' has been found to be cold tolerant to USDA Cold Hardiness Zone 6.

It is claimed:

1. A new and distinct variety of rose plant of the floribunda rose class named 'Poulpal021', illustrated and described herein as a distinct and novel rose variety due to its abundant red flowers, compact growth habit, disease resistance, and extended period of bloom.

* * * * *

'Poulpal021'